United States Patent [19]

Karasawa

[11] Patent Number: 4,776,336
[45] Date of Patent: Oct. 11, 1988

[54] RESECTOSCOPE

[75] Inventor: Hitoshi Karasawa, Hachioji, Japan

[73] Assignee: Olympus Optical Co., Ltd., Tokyo, Japan

[21] Appl. No.: 101,540

[22] Filed: Sep. 28, 1987

[30] Foreign Application Priority Data

Oct. 30, 1986 [JP] Japan .......................... 61-167216[U]

[51] Int. Cl.$^4$ .............................................. A61B 17/36
[52] U.S. Cl. ...................................... 128/303.15; 128/7
[58] Field of Search ........................ 128/4, 6, 7, 303.15

[56] References Cited

U.S. PATENT DOCUMENTS

| | | | |
|---|---|---|---|
| 4,132,227 | 1/1979 | Ibe .............................. | 128/303.15 X |
| 4,149,538 | 4/1979 | Mrava et al. .................. | 128/303.15 |
| 4,423,727 | 1/1984 | Widran et al. ................. | 128/303.15 |
| 4,538,610 | 9/1985 | Kubota ........................... | 128/303.15 |
| 4,643,187 | 2/1987 | Okada ........................... | 128/303.15 |
| 4,726,370 | 2/1988 | Karasawa et al. ............. | 128/303.15 |

Primary Examiner—William H. Grieb
Attorney, Agent, or Firm—Armstrong, Nikaido, Marmelstein & Kubovcik

[57] ABSTRACT

A resectoscope comprising a sheath body having an elongated hollow sheath to be inserted into a urethra, a handle having a guide part for guiding an optical sighting tube and a slider sliding in the axial direction along the sheath body. An optical sighting tube for observation is inserted through the guide pipe of the handle and is inserted within the sheath. An electrode inserting hole is provided in the slider and opens on the front surface of the slider and an electrode device removably inserted and connected in the electrode inserting hole, is inserted within the sheath. The electrode has a tip electrode which projects out of and retracts into the sheath by means of the movement of the slider in the axial direction. A step is formed between the guide pipe and the electrode inserting hole on the front surface of the slider, the step having the step surface connecting the two surfaces forming the step. The step surface is arcuate in the direction around an axis parallel with the axial direction of the electrode device.

10 Claims, 4 Drawing Sheets

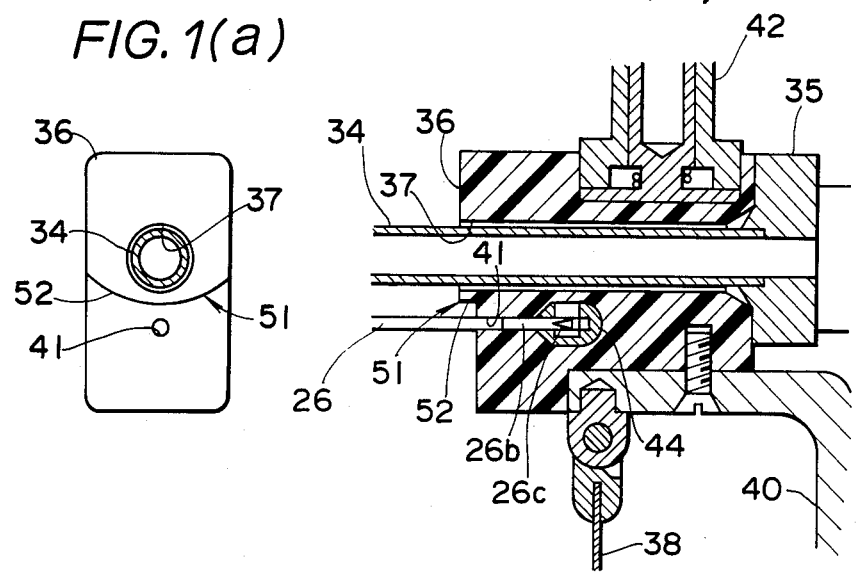
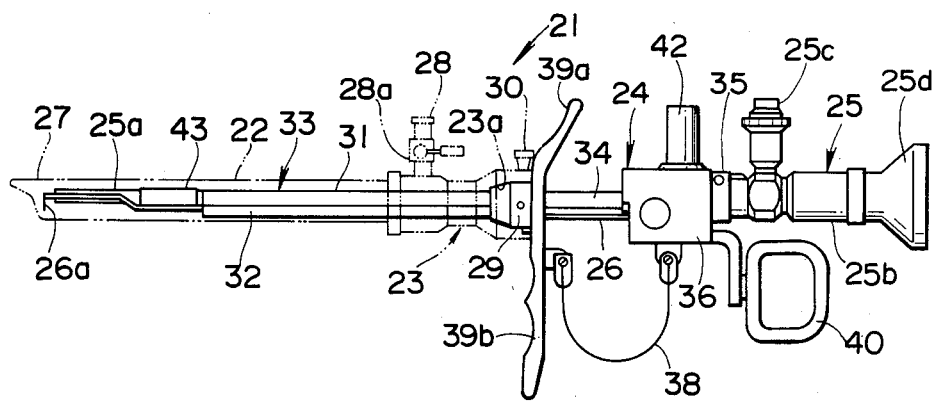

RESECTOSCOPE

BACKGROUND OF THE INVENTION

This invention relates to a resectoscope in which high frequency current leakage caused by a water drop between an electrode and a guide pipe is prevented by inhibiting the water drop from being deposited.

Recently extensive use has been made of an endoscope in which a body cavity interior can be observed and a curing treatment can be made by using an instrument in the endoscope without requiring an incision into the body. This is done by inserting an elongated insertable part into the body cavity. An example of the above-mentioned endoscope, is shown in U.S. Pat. No. 4,149,538, which discloses a resectoscope which can be inserted through a urethra to resect a swollen prostate or the like.

The above-mentioned resectoscope has a sheath body having an elongated sheath which is inserted into a urethra, a handle having a slider removably fitted into the rear end of the sheath body and an optical sighting tube for observation which is removably fitted from the rear end of the handle. An electrode device for resecting a prostate is inserted through the sheath and is fixed at the rear end to the slider so that, by operating the slider, the top of the electrode device projects out of or is retracted into the front end of the sheath.

FIG. 9 shows a slider of a resectoscope of such a device. FIG. 9(a) is an elevation of the slider and FIG. 9(b) is a sectioned view of the slider.

As shown in the drawings, the slider 1 is provided longitudinally with a guide pipe hole 3 through which a guide pipe 2 which is also a slider guide is to be inserted. An electrode inserting hole 4 is provided on the front surface of the slider parallel with the guide pipe hole 3. A water-tight O-ring 5 and an O-ring pressing member 6 are fitted into the inlet portion of the electrode inserting hole 4. A guide member 7 for guiding an electrode fixing member (not shown) is positioned and fixed in the deep portion of the electrode inserting hole 4. In this example, the slider 1 has a flat front surface.

FIG. 10 shows a slider of a resectoscope of another related example. FIG. 10(a) is an elevation of the slider and FIG. 10(b) is a sectioned view of the slider.

As shown in the drawings, a linear step 8 projects forward on the guide pipe hole 3 side and is positioned between the guide pipe hole 3 and electrode inserting hole 4 on the front surface of the slider 1. Thus, when the slider 1 is moved forward, the electrode inserting hole 4 is not in close contact with the rear end of the sheath connecting member of a resecting handle.

In a conventional resectoscope, as shown in FIG. 11, a water drop 11 is likely to be deposited so as to electrically connect the guide pipe 2 and an electrode device 10 in the part enclosed with the guide pipe 2 or the linear step 8. The electrode 10 is inserted in the electrode inserting hole 4 in the front surface of the slider 1. Therefore, there has been a problem in that high frequency current is likely to leak into the guide pipe 2 from the electrode inserting hole 4 through the water drop 11.

SUMMARY OF THE INVENTION

An object of the present invention is to provide a resectoscope wherein a high frequency current leakage caused by a water drop, can be prevented by inhibiting the water drop from being deposited between an electrode and a guide pipe on the front surface of a slider of the resectoscope.

This invention relates to a resectoscope comprising a sheath body having an elongated hollow sheath for insertion into a urethra, a handle having a guide pipe for guiding an optical sighting tube and a slider which slides in the axial direction along the guide pipe which is connected to the sheath body. An optical sighting tube is inserted through the guide pipe of the handle part and is inserted within the sheath. An electrode inserting hole is provided in the slider and opens on the front surface of the slider. An electrode device is removably inserted and connected in the electrode inserting hole, in the sheath and has a tip electrode projecting out of and retracting into the above sheath tip by means of the movement of the slider in the axial direction thereof. A step is provided between the guide pipe and the electrode inserting hole on the front surface of the slider. The step surface connects the two surfaces forming the step and is formed to be arcuate in the direction around an axis parallel with the axial direction of the electrode device.

BRIEF DESCRIPTION OF THE DRAWINGS

FIGS. 1 to 3 show a first embodiment of the present invention.

FIG. 1(a) is an elevation of a slider thereof.

FIG. 1(b) is a sectioned view of the slider.

FIG. 2 is a side view showing an entire resectoscope.

FIG. 3 is an explanatory view showing the state of a water drop in this embodiment.

FIGS. 4 and 5 show a second embodiment of the present invention.

FIG. 5 is an explanatory view showing the state of a water drop in this embodiment.

FIG. 6 shows a third embodiment of the present invention.

FIG. 7 shows a fourth embodiment of the present invention.

FIG. 8 shows a fifth embodiment of the present invention.

FIG. 9 shows a related example.

FIG. 10 shows another related example.

DETAILED DESCRIPTION OF THE PREFERRED EMBODIMENTS

Figure 3:
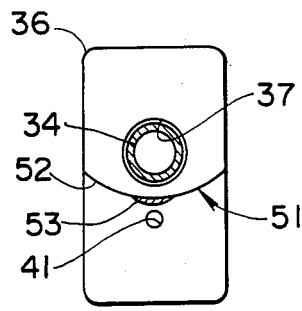

FIGS. 1 to 3 show the first embodiment of the present invention.

As shown in FIG. 2, a resectoscope 21 comprises a sheath body 23 having a hollow sheath 22 indicated by the two-point chain lines, a handle 24 connected to the sheath body 23, an optical sighting tube 25 inserted through the sheath 22 from the handle 24 and a bar-like electrode device 26 inserted from the handle 24 through the sheath 22.

The sheath 22 is elongated so as to be insertable into a human or animal body part such as the urethra and is provided with an insulating beak 27 connected to the tip. The sheath 22 may be formed integrally with the insulating beak which is made of an insulating material. The sheath body 23 has a water feeding port 28 provided with a cock 28a for feeding an irrigating liquid into a bladder through the sheath 22. The sheath body 23 also has a fitting port 23a into which a connecting member 29 of the handle 24 can be fitted and fixed and the sheath body 23 is provided with a removable fitting button 30 for removably fitting, for example, a clicking mechanism for fixing the connecting member 29 in the fitting part 23a.

A handle inserting part 33 has an optical sighting tube guide 31 through which the insertable part 25a of the optical sighting tube 25 is inserted into the handle 24. Further, the handle 24 has inserted therein an electrode guide tube 32 through which the electrode device 26 is inserted and is connected to the connecting member 29. The electrode guide tube 32 is also inserted into the sheath 22. A guide pipe 34 which is also a guide for the slider 36 is coupled to connecting member 29 and projects rearward in the axial direction. An optical sighting tube connecting part 35 is formed at the rear end of the guide pipe 34. The slider 36 slides in the axial direction along the guide pipe 34 between the connecting member 29 and optical sighting tube connecting part 35. The slider 36 is made of an insulating material such as a resin and is provided in the axial direction with a guide pipe hole 37 through which the guide pipe 34 is inserted as shown in FIG. 1(b). This slider 36 is biased by a spring 38 provided between the slider 36 and the connecting member 29 to maintain contact with, for example, the rearward optical sighting tube connecting part 35. The spring 38 is a plate spring in the disclosed embodiment but may be a coil spring or the like. The handle connecting member 29 is provided with finger portions 39a and 39b above and below the axis. The slider 36 is provided with a finger ring 40 on the rear lower part thereof.

As shown in FIGS. 1(a) and 1(b), an electrode inserting hole 41 in which the electrode device 26 is to be inserted and fixed is formed on the front surface of the slider 36. A connector 42 is positioned on top of the slider 36 to transmit a high frequency current from a high frequency cauterizing current source (not shown) to the electrode device 26.

The electrode device 26 projects forward through an inserting hole formed through the connecting member 29 of the handle 24 and the electrode guide tube 32. A resecting tip electrode 26a in the form of a loop, for example, is formed at the top of the electrode device 26. By transmitting a high frequency current to the tip electrode 26a, resecting or incising of a body part (such as a prostate) or the stopping bleeding in a bleeding part can be effected. A stabilizer 43 through which the insertable part 25a of the optical sighting tube 25 can be inserted is fitted on electrode device 26.

The optical sighting tube 25 can be removably inserted and connected in the optical sighting tube connecting part 35 of the handle 24. The connected optical sighting tube 25 is inserted through the optical sighting tube guide tube 31 which extends from the optical sighting tube connecting part 35 and connecting member 29 so that the tip side of the insertable part 25a projects out of the gurde tube 31. In the disclosed embodiment, the rearward extending part of the optical sighting tube guide tube 31 is the guide pipe 34. The guide pipe 34 is also a guide shaft for the slider 36. The guide shaft may, however, be provided separately from the guide pipe. The optical sighting tube 25 is formed of a body 25b, a forward connected elongated insertable part 25a, a light guide connector 25c and an eyepiece 25d. A light guide fiber transmitting an illuminating light to the tip of the insertable part 25a and an image transmitting optical system transmitting an observed image to the eyepiece 25d from the tip of the insertable part 25c are arranged within this optical sighting tube 25.

As shown in FIG. 1(b), near the rear end of the electrode device 26, the insulating coating is removed to expose a conductor part 26b. The deep portion of the electrode inserting hole 41 is expanded to hold and fix a guide member 44 for guiding an electrode fixing member (not shown). A groove 26c is made near the rear end of the conductor part 26b of the electrode device 26. The electrode fixing member (not shown) is guided by the guide member 44 from the side of the slider 36 to be engaged with the groove 26c to fix the electrode device 26.

In the embodiment shown in FIG. 1(b), a step 51 is formed between the guide pipe hole 37 and electrode inserting hole 41 on the front surface of the slider 36. As shown in FIG. 1(a), the step surface 52 connecting the two surfaces forming the step part 51 is arcuate around an axis parallel with the axial direction of the electrode device and is formed as a convex arc towards the electrode inserting hole 41.

According to this embodiment, a water drop will be divided by the step 51 formed between the guide pipe hole 37 and electrode inserting hole 41 on the front surface of the slider 36. Also, as shown in FIG. 3, a water drop 53 deposited on the step surface 52 of the step 51 will expand on the step surface 52 to an arcuate shape and will, therefore, flow away from the electrode device 26 side and will not drop on the electrode inserting hole 41 side. Therefore, on the front surface of the slider 36, the water drop 53 will be inhibited from being deposited in a manner to connect the guide pipe 34 and the electrode device 26 which is inserted in the electrode inserting hole 41 and thus, the leakage of a high frequency current through the water drop will be prevented.

Figure 4A:
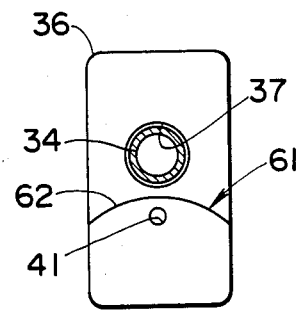
FIG. 4(a) is an elevation of a slider thereof.
Figure 4B:
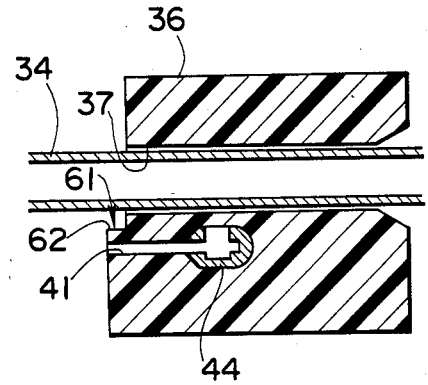
FIG. 4(b) is a sectioned view of the slider.
Figure 5:
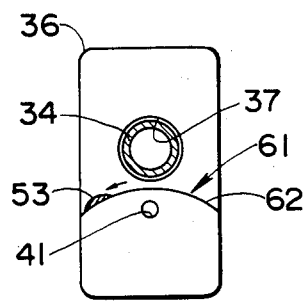

FIGS. 4(a), 4(b) and 5 show a second embodiment of the present invention. The connector 42, spring 38 and finger hanging ring 40 are omitted from these figures and the figures for the other embodiments described below.

In this embodiment, a step 61 which projects forward on the electrode inserting hole 41 side is formed between the guide pipe hole 37 and electrode inserting hole 41 on the front surface of the slider 36. The step surface 62 of the step 61 is formed to be a convex arc on the guide pipe hole 37 side.

According to this embodiment, a water drop will be divided by the step 61 and the water drop 53 deposited on the step surface 62 of the step 61 will flow sidewise along the step surface 62 away from the electrode device 26 as indicated by the arrow in FIG. 5. Therefore, on the front end surface of the slider 36, the water drop 53 will be inhibited from being deposited in a position to connect the guide pipe 34 and the electrode device 26 inserted in the electrode inserting hole 41.

Figure 6A:
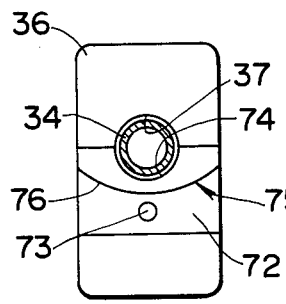
FIG. 6(a) is an elevation of a slider thereof.
Figure 6B:
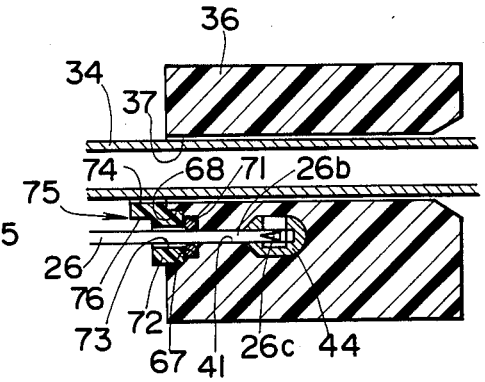
FIG. 6(b) is a sectioned view of the slider.

FIGS. 6(a) and 6(b) show a third embodiment of the present invention.

In this embodiment, a groove 67 of a circular cross-section and a groove 68 wider and laterally longer than the groove 67 are formed in the inlet portion of the electrode inserting hole 41. An O-ring 71 is positioned in the groove 67 and maintains water-tightness when the electrode device 26 is inserted into the electrode inserting hole 41. An O-ring pressing member 72 made, for example, of a resin for pressing the O-ring 71, is fitted in the groove 68. An electrode inserting hole 73 corresponding to the electrode inserting hole 41 is provided through the O-ring pressing member 72. The O-ring pressing member 72 projects on the front side from the front surface of the slider 36. A semicircular cut part 74 corresponding to the guide pipe hole 37 is formed in the upper end part of the projecting part. A step 75 projects forward on the cut part 74 side and is formed between the electrode inserting hole 73 and cut part 74 on the front end surface of the O-ring pressing member 72. The step surface 76 of the step 75 is formed to be a convex arc on the electrode inserting hole 73 side.

The function and effect of this embodiment is the same as that of the first embodiment.

Figure 7A:
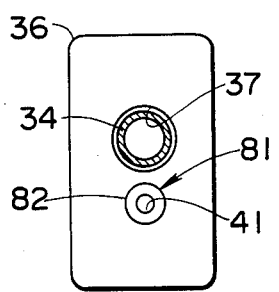
FIG. 7(a) is an elevation of a slider thereof.
Figure 7B:
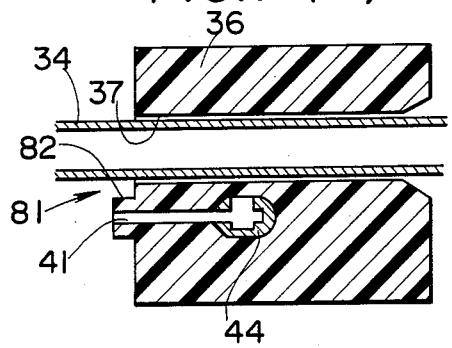
FIG. 7(b) is a sectioned view of the slider.

FIGS. 7(a) and 7(b) show a fourth embodiment of the present invention.

In this embodiment, a thick-walled cylindrical projection 81 with the electrode inserting hole 41 as a center thereof is formed around the opening of the electrode inserting hole 41 on the front surface of the slider 36. A step is formed by the projection 81 between the guide pipe hole 37 and electrode inserting hole 41 on the front surface of the slider 36.

According to this embodiment, the step formed by the projection 81 causes a water drop to be divided and the water drop is deposited on the side surface 82 of the projection 81 and will easily flow downward along the side surface 82. Therefore, on the front surface of the slider 36, the water drop will be inhibited from being deposited thus preventing the connection of the guide pipe 34 and the electrode device 26 inserted in the electrode inserting hole 41.

The projection 81 is not limited to a thick-walled cylindrical projection around the above-mentioned electrode inserting hole 41.

Figure 8A:
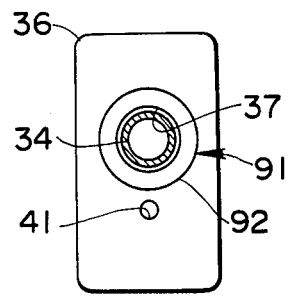
FIG. 8(a) is an elevation of a slider thereof.
Figure 8B:
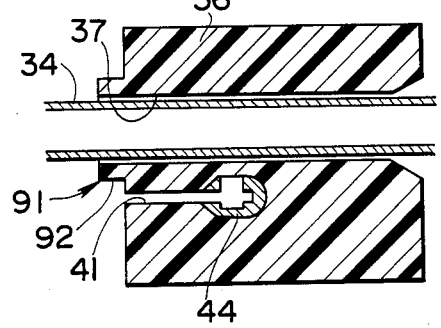
FIG. 8(b) is a sectioned view of the slider.
Figure 9A:
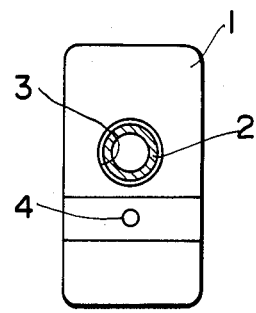
FIG. 9(a) is an elevation of a slider thereof.
Figure 9B:
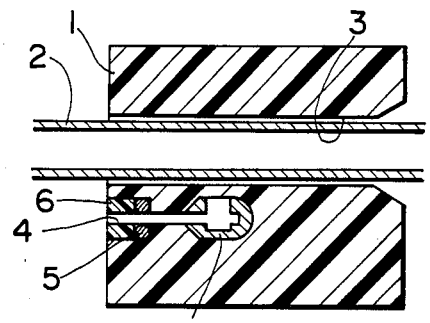
FIG. 9(b) is a sectioned view of the slider.
Figure 10A:
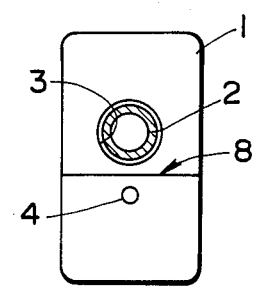
FIG. 10(a) is an elevation of a slider thereof.
Figure 10B:
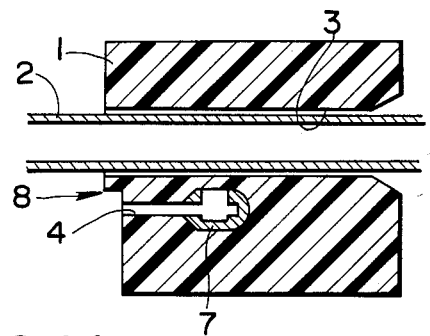
FIG. 10(b) is a sectioned view of the slider.
Figure 11:
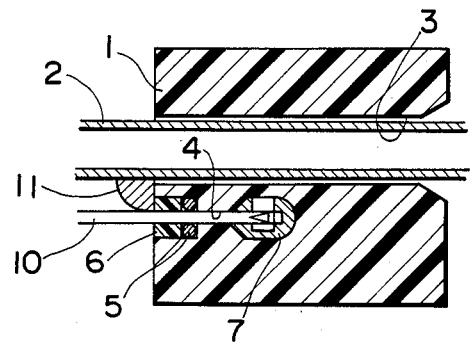
FIG. 11 is an explanatory view showing the state of a water drop in the related example.

FIGS. 8(a) and 8(b) show a fifth embodiment of the present invention.

In this embodiment, a thick-walled cylindrical projection 91 with the guide pipe hole 37 as a center, is formed around the opening of the guide hole 37 on the front end surface of the slider 36. A step is formed by projection 91 between the guide pipe hole 37 and electrode inserting hole 41 on the front surface of the slider 36.

According to this embodiment, a water drop will be divided by the step formed by the projection 91 and the water drop deposited on the side surface 92 of the projection 91 will expand on the side surface and will not drop on the electrode inserting hole 41 side.

The present invention is not limited to only the above described embodiments. For example, in the fourth or fifth embodiment, the projection 81 or 91 may be a member which is separate from the slider 36.

As explained above, according to the present invention, step is provided between the guide pipe and the electrode inserting hole, such that a water drop will be divided by the step. As the step surface is formed to be arcuate, the water drop will expand on the step surface, will easily flow sidewise and will flow away from the electrode device side. Therefore, a water drop can be inhibited from being deposited in a position to connect the electrode device and guide pipe with each other on the front surface of the slider.

The present invention may be embodied in other specific forms without departing from the spirit or essential characteristics thereof. The presently disclosed embodiments are therefore to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed is:

1. A resectoscope comprising:
   a sheath body having an elongated hollow sheath for insertion into a human or animal body;
   a handle having a guide pipe for guiding an optical sighting tube and a slider for sliding in the axial direction along said guide pipe, said guide pipe being connected to said sheath body;
   an optical sighting tube inserted through said guide pipe of said handle and inserted within said sheath;
   an electrode inserting hole formed in said slider and opening on the front surface of said slider;
   an electrode means removably inserted and connected in said electrode inserting hole, said electrode means being inserted within said sheath and having a tip electrode projecting out of and retractable into said sheath by the movement of said slider in the axial direction; and
   a step formed on the front surface of said slider between said guide pipe and said electrode inserting hole, said step having a step surface connecting the two surfaces forming said step, wherein said step surface is arcuate around an axis parallel to the axial direction of said electrode means.

2. A resectoscope according to claim 1, wherein said step projects forward on said guide pipe side and said step surface is a convex arc on said electrode inserting hole side.

3. A resectoscope according to claim 1, wherein said step projects forward on said electrode inserting hole side and said step surface is a convex arc on said guide pipe side.

4. A resectoscope according to claim 1, including an O-ring on the inlet portion of said electrode inserting hole for maintaining water-tightness of said electrode inserting hole when said electrode means is inserted therein.

5. A resectoscope according to claim 4, wherein said step is formed in the front portion of a means for pressing said O-ring.

6. A resectoscope according to claim 5, wherein said step projects forward on said guide pipe side and said step surface is a convex arc on said electrode inserting hole side.

7. A resectoscope according to claim 1, wherein said step is a thick-walled cylindrical projection formed around the opening of said electrode inserting hole.

8. A resectoscope according to claim 1, wherein said step is a thick-walled cylindrical projection formed around said guide pipe on the front surface of said slider.

9. A resectoscope according to claim 1, wherein said guide pipe is a guide means for said slider.

10. A resectoscope comprising:
- a sheath body having an elongated hollow sheath for insertion into a human or animal body;
- a handle having a guide pipe for guiding an optical sighting tube and a slider means for sliding in the axial direction along said guide pipe, wherein said handle is connected to said sheath body;
- an optical sighting tube inserted through said guide pipe and inserted within said sheath;
- an electrode inserting hole provided in said slider means, wherein said electrode inserting hole opens on the front surface of said slider means;
- an electrode means removably connected in said electrode inserting hole, said electrode means being positioned within said sheath and having a tip electrode projecting out of and retractable into said sheath by the movement of said slider means in the axial direction; and
- a step means formed between said guide pipe and said electrode inserting hole on the front surface of said slider means, wherein said step means has an arcuate convex step surface connecting the two surfaces forming said steps.

* * * * *